United States Patent [19] [11] 4,242,256
Sharpe et al. [45] Dec. 30, 1980

[54] SYNTHESIS OF PEPTIDE ANALOGUES

[76] Inventors: Robert Sharpe, 64 Cleveland Rd., Ealing, London W13; Michael Szelke, 10 North Dr., Ruislip, Middlesex, both of England

[21] Appl. No.: 53,519

[22] Filed: Jun. 29, 1979

Related U.S. Application Data

[63] Continuation of Ser. No. 886,789, Mar. 15, 1978, abandoned, which is a continuation-in-part of Ser. No. 780,436, Mar. 23, 1977, abandoned.

[30] Foreign Application Priority Data

Mar. 15, 1977 [GB] United Kingdom ............... 13192/76

[51] Int. Cl.³ ................. C07C 103/52; C07D 207/24; C07C 147/02; C07C 101/30
[52] U.S. Cl. .......................... 260/112.5 R; 260/326.2; 562/567; 562/571; 562/568; 562/442; 562/560; 562/561; 562/556
[58] Field of Search ................. 260/112.5 R; 562/567, 562/568, 571, 442, 560, 561, 556

[56] References Cited

PUBLICATIONS

Harper, "Review of Physiological Chemistry", Edition 13, (1971), 390–391.

*Primary Examiner*—Delbert R. Phillips
*Attorney, Agent, or Firm*—Oblon, Fisher, Spivak, McClelland & Maier

[57] ABSTRACT

Compounds being analogues of a dipeptide in which the nitrogen atom of the linking amide group of the dipeptide is replaced by trivalent group

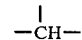

and in which, optionally, the carbonyl function of this linking group is replaced by the divalent group $-CH_2-$ are of value in the synthesis of isosterically modified peptides.

19 Claims, No Drawings

SYNTHESIS OF PEPTIDE ANALOGUES

This is a continuation of application Ser. No. 886,789, filed Mar. 15, 1978, which is a continuation-in-part of Ser. No. 780,436, filed Mar. 23, 1977, both now abandoned.

This invention relates to the synthesis of peptide analogues and to intermediates for use therein.

Modification of one or more of the amino acid linkages of a physiologically active peptide through replacement with an isosteric group can lead to an improvement in the properties of the peptide. Thus, for example, it may be possible to increase the stability of the peptide in vivo without detracting to an unacceptable extent from its physiological action, as described by Parry et al in Chemistry and Biology of Peptides, Ann Arbor, 1972, 541, for the isosteric replacement —CONH—→—CH$_2$NH—. We have now discovered certain novel and quite different forms of isosteric replacement for use in peptides having advantages compared with the use of the group —CH$_2$NH— of Parry et al, and describe herein dipeptide analogues for use in the synthesis of such isosterically modified peptides.

Accordingly the present invention comprises a compound being an analogue of a dipeptide in which the nitrogen atom of the linking amide group of the dipeptide is replaced by the trivalent group

and in which, optionally, the carbonyl function of the linking group is replaced by the divalent group —CH$_2$—.

The term dipeptide is used herein to indicate a compound formed by the linkage of two amino acids, ie of two acids each containing both an amino and a carboxy group, through the formation of an amide linkage, and extends to compounds in which the terminal amino and/or carboxyl group is in the form of a derivative thereof as well as to compounds containing free terminal amino and carboxyl groups.

Dipeptide analogues according to the invention include various compounds of formula R$^1$R$^2$N.X.CH$_2$CHR.Y.COR$^3$ and of formula R$^1$R$^2$N.X.COCHR.Y.COR$^3$, wherein X and Y are the same or different organic groups, R is an organic group or a bond to the group Y forming a cyclic group

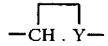

and particularly hydrogen, NR$^1$R$^2$ is an amino group or an imino group bonded to the group X forming a cyclic group

or a derivative of such amino or imino group, and COR$^3$ is a carboxyl group or a derivative thereof. However, the compounds of most interest are analogues of those dipeptides which derive from two α-amino acids, X being a group —CH(R$^4$)— in which R$^4$ is hydrogen, a monovalent organic group or a divalent organic group bonded to the group R$^1$R$^2$N— and Y is a group —CH(R$^5$)— in which R$^5$ is hydrogen, a monovalent organic group or a divalent organic group bonded to the group

the two former alternatives being preferred.

Compounds of particular interest are analogues of those dipeptides which derive from the naturally occurring α-amino acids (the term amino acids as used herein in a general sense extends to imino acids). However the dipeptides may be derived not only from the L-isomers of naturally occurring acids but from the L- and D-isomers of both these and other acids which are not naturally occurring. It will be appreciated that even among the naturally occurring acids a wide variety of structures is found, the organic groups R$^4$ and R$^5$ being, for example, a straight-chain, branched or cyclic (carbo- or hetero-) group (the last mentioned only, with R$^1$R$^2$N- or

in the case of divalent groups) which may contain carboxyl, amino, imino, hydroxyl, sulphydryl, benzyl, phenyl, indolyl, imidazolyl and pyrrolidyl substituents, etc. Specific amino acids include alanine (i.e. α-alanine), β-alanine, arginine, asparagine, aspartic acid, 3,5-dibromotyrosine, cystine, cysteine, dopa, N-formylglycine, glycine, glutamic acid, glutamine, histidine, hydroxylysine, hydroxyproline, 3,5-diiodotyrosine, isoleucine, leucine, lysine, methionine, ornithine, phenylalanine, proline, pyroglutamic acid, hydroxyproline, serine, spinacin, threonine, thyroxine, tryptophan, tyrosine and valine, as well as derivatives of N-formylglycine, glutamic acid, glutamine and pyroglutamic acid in which the α-amino group carries a lower alkyl (C$_1$ to C$_4$) substituent, for example methyl.

Examples of groups of compounds of a particular type according to the present invention are those in which the central group (—CH$_2$CHR— or —COCHR—) in the formulae above is an ethylene group or a group —COCH$_2$—, respectively, or to a lesser extent a group

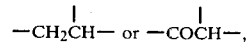

respectively linked to the group Y, preferred compounds being those in which the C-terminal portion of the molecule corresponds to derivation from an amino acid as opposed to an imino acid in which the imino group is part of a cyclic group, this portion of the molecule being derived, for example, from glycine.

Specific examples of dipeptide analogues according to the present invention are those derived from the above listed amino acids by combination thereof either with a similar amino acid or in pairs of different amino acids in either order (i.e. at the C- or N-terminus), including compounds in which the amino and/or carboxy group is present in functional derivative form. Among these analogues may be mentioned compounds which may be regarded as derived from the following dipeptides by replacement of the central —CONH— group thereof by the group —CH$_2$CH$_2$— or the group —COCH$_2$— (particularly when the individual amino acid residues where enantiomorphic are of the L-configuration) arginyl-proline, histidyl-trypthophan, pyroglutamyl-histidine, seryl-tyrosine, trypthophanyl-serine, tyrosyl-alanine (the L-tyrosyl-D-alanine also being of some particular interest in this instance) and particularly leucyl-arginine, glycyl-leucine, and also phenylalanyl-glycine, prolyl-glycine and tyrosyl-glycine, and functional derivatives thereof.

The dipeptide analogues according to the present invention are most conveniently prepared either by constructing the C-terminal portion of the molecule upon the N-terminal portion of the molecule as a starting material or by attachment of suitable precursors for these two portions, rather than by any attempt to modify the dipeptide as such.

Analogues of the general formula R$^1$R$^2$N.X.CH$_2$CHR.Y.COR$^3$ in which the C-terminal moiety is the grouping .CH$_2$.CH$_2$.CO$_2$H are preferably prepared by effecting the introduction in turn into the amino acid corresponding to the N-terminal moiety of the analogue of three methylene groups. conveniently by use of the series of reactions known as the Arndt-Eistert synthesis comprising formation of the diazoketone followed by rearrangement thereof to the carboxylic acid or an ester thereof.

The N-terminal amino acid is conveniently used in the form of the N-protected compound. Various N-protecting groups may be used which will remain in place dring the various stages of the synthesis, suitable groups being selected, for example, from the N-protecting groups described in the literature of peptide chemistry. In general, however, it is preferred to use a bi-functional protecting group, for example phthaloyl, where the N-terminus is derived from an amino rather than an imino acid and has a —NH$_2$ rather than a —NH— group. Alternatively, however, and particularly where the N-terminus does have a —NH group, as for example in proline, mono-functional protecting groups may be used, which like the bi-functional groups may also be hydrogenolysable or hydrolysable under acidic or alkaline conditions for removal thereof, for example an aralkyloxy- or alkyloxy-carbonyl group such as benzyloxycarbonyl or ethoxycarbonyl.

The terminal N-terminal amino acid may conveniently be used in the Arndt-Eistert synthesis in the form of an acid halide such as the acid chloride or bromide, or the imidazoyl amide, or particularly as an anhydride which may be symmetrical or more especially mixed in order to reduce the amount of the amino acid required. Particularly suitable mixed anhydrides are those formed with acids which are such that the amino acyl carbonyl group is then preferentially attacked by nucleophiles, for example those acids containing sterically hindered groups such as pivalic acid and also those formed with alkoxy formic acids such as isobutoxyformic acid. Reaction with diazomethane is directed predominantly to the amino acid part of the mixed anhydride by steric factors in the case of an anhdride with an acid such as pivalic acid, and by electronic factors in the case of anhydride with an acid such as isobutoxyformic acid.

Following reaction with diazomethane to give the diazoketone, this compound is conveniently treated with a suitable alcohol in the presence of an appropriate catalyst, for example silver oxide, to form the corresponding ester, which is then converted to the free acid for two repetitions of this whole procedure. It is convenient to use an alcohol such as benzyl alcohol to give an ester which may be converted to the free acid by catalytic hydrogenation. Alternatively the ester may be hydrolysed, for example by acid hydrolysis in some medium such as aqueous hydrochloric acid/acetic acid, in which case various alochols may be used, for example a lower alkanol of 1 to 5 carbon atoms such as methyl alcohol, ethyl alcohol, propyl alcohol, t-butyl alcohol and isoamyl alcohol. Indeed, in some cases it may be found that hydrolysis is to be preferred to hydrogenolysis owing to the difficulty of removing the benzyl group in some compounds.

The advantage of the method described above employing the Arndt-Eistert synthesis is that the method is well suited by the retention of configuration at the carbon atom to which the amino group of the N-terminal amino acid is joined. In the case of the dipeptide analogues of the general formula R$^1$R$^2$N.X.CH$_2$CHR.Y.COR$^3$ in which the C-terminal moiety derives from an amino acid other than glycine, synthesis of the analogues is complicated by the presence of an additional asymmetric carbon atom. Two alternative methods for the synthesis of such analogues are shown below. These methods are, of course, also applicable to the case where the C-terminal moiety derives from glycine but are usually less preferred than the previously described method in this instance. It will be seen that these methods also lead to the formation of analogues of the general formua R$^1$R$^2$N.X.COCHR.Y.COR$^3$, these being of interest firstly as intermediates for the preparation of analogues of the general formula R$^1$R$^2$N.X.CH$_2$CHR.Y.COR$^3$ and secondly, in their own right, for the synthesis of isosterically modified peptides.

Method 1

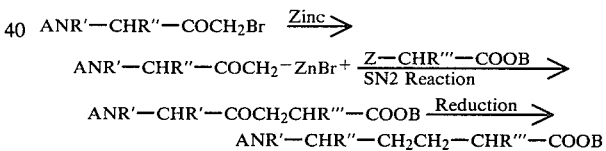

Method 2

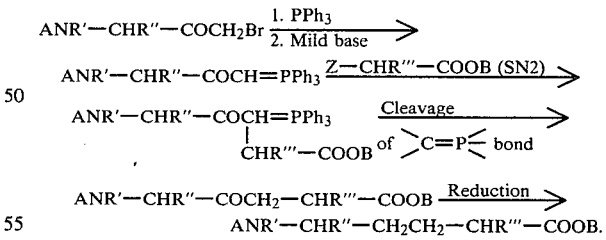

wherein R' represents hydrogen or a bond to R", R" represent hydrogen, a monovalent organic group or a divalent organic group joined to AN—, R''' represents hydrogen or a monovalent organic group, A nd B represent suitable protecting groups, and Z represents a suitable leaving group in the SN2 reaction.

The synthetic methods described above are suited to the retention of configuration at one or both of the carbon atoms to which the amino groups of the amino acids are joined, resolutions being employed if configuration is lost at one centre. In the first method a haloketone is treated with a suitable metal, for example zinc, in an aprotic, highly polar solvent, for example hexamethyl phosphoramide or particularly dimethyl sulphoxide in benzene, to thereby lead to the selective formation of the appropriate enolate. The resulting carbon ion is reacted by an SN2 pathway with the reactant Z-CHR'''-COOB which is obtained without racemisation from the corresponding amino acid, suitable leaving groups Z being the tosylate (p-toluene sulphonate) and bromide anions. Reduction of the keto group may then be effected, for example as described below.

In the second method a haloketone is treated with triphenylphosphine under appropriate conditions to form the phosphonium halide salt which on treatment with a mild base, for example $Na_2CO_3/H_2O/C_2H_5OCOCH_3$, yields a ylide. Reaction with the reactant Z-CHR'''-COOB, as described above, effects introduction of the group —CHR'''-COOB at the carbon atom of the C=P bond of the ylide and this is followed by cleavage of this bond. The presence of the adjacent keto group stabilises the bond, however, and for this reason the use of electrolysis is preferred to effect the cleavage by reduction rather than a hydrolytic method, the cleavage of ylides by such electrolytic methods being well known in the art. Reduction of the keto group to afford the second type of analogue may be effected by various procedures known in the art. Procedures such as reaction with $HSCH_2CH_2SH$ followed by treatment with Raney nickel can be complicated by the effect of the Lewis acid used in the dithiol reaction on some of the more common N-protecting groups such as t-butoxycarbonyl. Accordingly, it is preferable in order to avoid the necessity for the use of other forms of protecting group, to use a stepwise reduction procedure involving conversion of the grouping —COOB— to —COOH, reduction of the keto group to an alcohol, activation of the alcohol group, for example as a mesylate, tosylate etc, followed finally by the selective reduction of this activated group with a hydride reagent such as lithium aluminium hydride, these all being procedures well known in the art.

Suitable N-protecting groups A include various urethane N-protecting groups, particularly such as t-butoxycarbonyl etc. Suitable C-protecting groups B include various alkyl groups, particularly lower ($C_1$ to $C_4$) alkyl groups such as methyl and, indeed, it may even be possible in certain instances to simplify the procedure by using a free carboxy group. Protection of functional groups in R'' and R3' by conventional procedures may also be necessary. The α-haloketones are readily obtainable from the corresponding diazoketones, for example by treatment with HBr at $-10°$ C. The various reactions involved in methods 1 and 2 all involve standard procedures and variations upon them, for example variations to make analogues containing a group —COCHR— and hence those containing a group —$CH_2$CHR—, will be apparent to those skilled in the art. Indeed, it will be appreciated that, in general, the methods of synthesis described herein are not the only ones which may be used for the preparation of the dipeptide analogues according to the present invention and that obvious chemical equivalents of these methods or other methods known in the art for effecting similar reactions and obvious chemical equivalents thereof may be employed.

The compounds having free amino and carboxy groups may be obtained by removal of the N-protecting group and also of the C-protecting group, where applicable, which have been used in their synthesis, the phthaloyl group, for example, being removed by acid hydrolysis. Where analogues of the general formula $R^1R^2N.X.COCHR.Y.COR^3$ are required as intermediates for the preparation of those of the general formula $R^1R^2N.X.CH_2CHR.Y.COR^3$, then such removal is usually best left until the end of the synthesis as shown under method 1 or method 2 above. However, where such analogues are required for the synthesis of larger peptide analogues containing a $$-COCH- \text{ group,}$$

then the synthesis will be interrupted at the penultimate stage shown and the removal of the protecting groups then carried out, where appropriate.

The dipeptide analogues according to the present invention may be used for the synthesis of larger peptide analogues by the addition of further amino acids or peptides thereto by exactly analogous procedures to those described in the literature of peptide chemistry for the addition of amino acids and peptides to dipeptides or amino acids. It will be appreciated, furthermore, that such larger peptide analogues may contain more than one amide bond modified as described herein. In many instances the dipeptide analogue used in such syntheses will be modified somewhat from that corresponding simply to the compound produced by the replacement of the amide link in a dipeptide derived from two amino acids by a group —$CH_2$CHR— or —COCHR—. Such modifications may already be incorporated into the dipeptide analogue produced by an appropriate method of synthesis as indicated above, or alternatively the analogue may be modified appropriately before use. A first type of modification is necessary where the amino acids from which the analogue derives contain groups which are normally protected during peptide syntheses. These groups will usually require to be protected in the dipeptide analogue and this protection may conveniently be effected by similar procedures to those described in the art of peptide chemistry. Examples of such groups in the commonly occurring amino acids are the ε-amino group of lysine and the sulphydryl group of cysteine, the β-carboxy group of aspartic acid and the γ-carboxy group of glutamic acid, the hydroxy group of serine, threonine and tyrosine, and less commonly the amide group of asparagine and glutamine, the sulphide group of methionine and the imino group of tryptophan. Secondly, it will often be necessary to modify the amino or imino group, or the carboxy group of the dipeptide analogue. This necessity will depend on the type of reaction in which the analogue is being used. Thus when an amino acid or peptide is being added to the N-terminus of the analogue it will be usual to protect the terminal carboxy group thereof when the C-terminus of the added amino acid or peptide is reacted as a free carboxy group using a suitable condensing agent such as dicyclohexylcarbodiimide. When the C-terminus of the added amino acid or peptide is reacted as an activated functional derivative thereof, then the terminal carboxy group of the dipeptide analogue may either be protected or may be present in zwitterion form or as a carboxylate salt. On the other hand, when an amino acid or peptide is being added to the C-terminus of the analogue it will be usual to protect the terminal amino or imino group thereof and, furthermore, it may also be appropriate to modify the carboxy group to activate it as described above as an alternative to using the free carboxy group with a suitable condensing agent.

Examples of suitable activating functional derivatives of the C-terminal carboxy group of the dipeptide analogue are active esters, mixed anhydrides, for example from isobutyl chlorocarbonate, the symmetrical anhydride, the azide and also masked azides such as the derivatives —NHNHS wherein S represents a t-butoxycarbonyl, benzyloxycarbonyl group, etc. Of these derivatives the active esters are of particular interest, for example the esters with p-nitrophenol, 2,4-dinitrophenol, 2,4,5-trichlorophenol, 2,3,4,5,6-pentachlorphenol, N-hydroxyphthalimide, N-hydroxysuccinimide, 5-chloro-8-hydroxyquinoline etc.

Examples of suitable protecting groups for the C-terminal carboxy group of the dipeptide analogues are groups removable both by hydrolytic and catalytic cleavage, particularly esters and amides, including N-substituted amides, for example various substituted benzyl esters and alkyl esters (for example $C_1$ to $C_4$) including the t-butyl ester. It will be appreciated that the carboxy group may also be protected through attachment to a resin in solid phase synthesis.

Examples of suitable protecting groups for the N-terminal amino of the dipeptide analogues are groups removed both by hydrolytic and catalytic cleavage including benzyloxycarbonyl and derivatives thereof such as p-methoxybenzyloxycarbonyl, amyloxycarbonyl, biphenyl isopropoxycarbonyl, o-nitrophenylsulphenyl, phthaloyl and t-butoxycarbonyl. In addition it is also possible in the case of these dipeptide analogues to use N-protecting groups such as acyl groups which are not normally used in peptide chemistry because of the tendency to cause racemisation at the α-carbon atom during coupling.

As indicated above, the dipeptide analogues may be used for the synthesis of a wide variety of peptides containing one or more amide linkages modified according to the present invention. Such peptides are prepared by the addition of one or more amino acids, peptides or dipeptide analogues according to the present invention to one or both of the N- and C-terminal ends of the dipeptide analogue using either classical, solution, methods or solid phase methods and effecting reaction between the appropriate terminus of the reactant and of the dipeptide analogue according to the general procedures indicated above. Thus a free-N-terminal amino group of the reactant may be reacted with the C-terminal carboxy group of a suitable derivative thereof on the dipeptide analogue or vice versa, other reactive groups in the reactant being appropriately protected as described above.

The invention is illustrated by the following Examples, Examples 1 to 7 relating to various dipeptide analogues and Example 8 being illustrative of how such analogues are incorporated into a larger peptide analogue.

EXAMPLES (All of the amino acids used herein are of the L-configuration where enantiomorphic and this configuration is retained in the products derived therefrom)

EXAMPLE 1: 5-AMINO-6-PHENYLHEXANOIC ACID (Analogue of phenylalanyl-glycine in which —$CH_2CH_2$— replaces—CONH—)

(1) 4-Phenyl-3-pthalimidobutanoic acid.

N-Methylmorpholine (0.60 mls, 5.42 mmoles) is added to a stirred solution of N-phthaloylphenylalanine (1.60 g, 5.42 mmoles) in dry ethyl acetate (15.00 mls). The solution is cooled to $-15°$ C., isobutylchloroformate (0.71 mls, 5.42 mmoles) is added dropwise and the mixture is kept at $-15°$ C. for 8 minutes. The suspension is filtered and the filtrate treated with a pre-cooled solution of diazomethane (12 mmoles) in dry ether (70 mls). The yellow solution is kept at 4° C. for 5.0 hours and then evaporated to afford the pure diazoketone as a yellow solid, $\nu_{max}$ ($CHCl_3$): 2115, 1780, 1720 $cm^{-1}$.

A solution of the diazoketone (100% of amount obtained) and dry benzyl alcohol (5.85 g, 54.2 mmoles) in dry dioxane (34 mls) is treated with silver oxide 0.25 g, 1.08 mmoles) and the suspension stirred and heated on an oil bath (70° C.) for 0.50 hour. The mixture is allowed to cool to room temperature, filtered, evaporated and the crude benzyl ester hydrogenolysed in methanol (35 mls) over palladium-charcoal catalyst (10% 0.20 g,) for 18 hours at room temperature and pressure. The reaction product is filtered, evaporated and redissolved in ethyl acetate (50 ml). Extraction with sodium bicarbonate (1 M, 3×25 ml) and acidification affords the free acid, 4-phenyl-3-phthalimido-butanoic acid as a white solid. Crystallisation from aqueous methanol affords the acid as a white powder (1.00 g, 60%), m.p. 123°–124.5° C.

(2) 5-Phenyl-4-phthalimidopetanoic acid.

N-Methylmorpholine (0.27 mls, 2.42 mmoles) is added to a stirred solution of 4-phenyl-3-phthalimidobutanoic acid (0.75 g, 2.42 mmoles) in dry ethyl acetate (7.50 mls). The solution is chilled to $-15°$ C., isobutylchloroformate (0.32 mls, 2.42 mmoles) is added dropwise and the mixture kept at $-15°$ C. for 8 minutes. The suspension is filtered and the filtrate treated with a pre-cooled solution of diazomethane (6 mmoles) in dry ether (40 mls), and kept at 4° C. for 18 hours. Evaporation affords the pure diazoketone as a yellow solid, $\nu_{max}$ ($CHCl_3$): 2110, 1775, 1710 $cm^{-1}$.

A solution of the diazoketone (90% of amount obtained) and dry benzyl alcohol (2.44 g, 22.60 mmoles) in dry dioxane (15 mls) is stirred with silver oxide (0.10 g, 0.45 mmoles) and heated on an oil bath (70° C.) for 0.50 hour. The suspension is allowed to cool to room temperature, filtered, evaporated and the crude benzyl ester hydrogenolysed in methanol (20 mls) over palladium charcoal catalyst (10λ. 0.09 g.) for 25 hours at room temperature and pressure. The mixture is filtered, evaporated and the residual oil is redissolved in ethyl acetate (25 ml). Extraction with sodium bicarbonate (1 M 3×10 ml) and acidification affords the free acid, 5-phenyl-4-phthalimidopentonaic acid, as a white solid which on crystallisation from aqueous methanol is obtained as a white powder (0.357 g, 50%), m.p. 142°–143.5° C.

Hydrogenolysis of the bicarbonate insoluble fraction affords a further quantity of the acid (0.050 g; total yield 0.407 g, 57%).

(3) Methyl 6-phenyl-5-phthalimidohexanoate.

N-Methylmorpholine (0135 mls, 12.37 mmoles) is added to a stirred solution of 5-phenyl-4- phthalimidopentanoic acid (0.40 g, 1.237 mmoles) in dry ethyl acetate (8.25 mls). The solution is cooled to $-15°$ C., isobutylchloroformate (0.16 mls, 1.237 mmoles) is added dropwise and the mixture is kept at $-15°$ C. for 8 minutes. The suspension is filtered and the filtrate treated with a pre-cooled solution of diazomethane (6 mmoles) in dry ether (40 mls), and kept at 4° C. for 48 hours. Evaporation affords the pure diazoketone as an oily solid max (CHCl$_3$): 2110, 1773, 1710 cm$^{-1}$.

A solution of the diazoketone (90% of amount obtained) in methanol (9.00 mls) is treated with silver oxide (0.052 g, 0.224 mmoles) and the suspension stirred and heated on an oil bath (70° C.) for 15 minutes. The product is allowed to cool to room temperature, filtered and evaporated to give crude methyl 6-phenyl-5-phthalimidohexanoate.

(4) 5-amino-6-phenylhexanoic acid.

Methyl 6-phenyl-5-phthalimidohexanoate (whole amount of crude material obtained) is dissolved in glacial acetic acid (2.50 mls). Analar hydrochloric acid (6 N, 12.00 mls) is added and the mixture is heated at 110° C. for 16.5 hours in six sealed tubes. The reaction product is extracted with ethyl acetate (6 × 10 mls) and the aqueous phase evaporated giving crude 5-amino-6-phenylhexanoic acid as the hydrochloride (0.235 g).

EXAMPLE 2:
5-t-BUTOXYCARBONYLAMINO-6-PHENYL-HEXANOIC ACID.

A solution of crude 5-amino-6-phenylhexanoic acid hydrochloride (0.235 g, 0.97 mmoles) prepared as described in Example 1 and tetramethylguanidine (0.438 g, 2.90 mmoles) in dimethylformamide (6.60 mls) is treated with t-butoxycarbonylazide (0.276 g, 1.93 mmoles) in dimethylformamide (3.00 mls) and the solution stirred for 48 hours at room temperature. The dimethylformamide is evaporated and the product partitioned between ethyl acetate and 1 M citric acid. Extraction of the organic phase with 3% aqueous ammonia followed by acidification and extraction affords 5-t-butoxycarbonylamino-6-phenylhexanoic acid, which is further purified by preparative t.l.c. using benzene-dioxane-acetic acid (95:25:4 v/v/v) for development. Elution with ethyl acetate affords the pure acid as a white solid (0.180 g, 53% based on 5-phenyl-4-phthalimidopentanoic acid). Crystallisation from ethyl acetate/petrol (60°–80° C.) gives the acid in the form of a white powder, m.p. 94.5°–96.5° C.; $\tau$(CDCl$_3$): $-0.67$ (1H, s,D$_2$O-exchangeable), 2.82 (5H,s), 5.58 br (1H, D$_2$O-exchangeable) 6.28 br (1H), 7.28 (2H,d, J=6.5H$_z$), 7.68 (2H multiplet), 8.05–8.90 (10H, complex); $\nu_{max}$ (CHCl$_3$): 2600 (very broad) 1710, 1500 cm$^{-1}$.

EXAMPLE 3:
5-AMINO-6-(4-HYDROXYPHENYL)HEXANOIC ACID.

(Analogue of tyrosyl-glycine in which —CH$_2$CH$_2$— replaces —CONH—)

The preparation of this compound is effected by a substantially similar procedure to that described for the corresponding phenylalanyl-glycine analogue of Example 1 but the 4-hydroxyphenyl group is protected during the synthesis by acetylation.

(1) 4-(4-Acetoxyphenyl)-3-phthalimidobutanoic acid.

O-Acetyl-N-phthaloyltyrosine (m.p. 176°–179° C., prepared in 81% yield by treating N-phthaloyltyrosine with acetic anhydride in pyridine; the N-phthaloyltyrosine being prepared in 91% yield from N-carbethoxyphthalimide, triethylamine and L-tyrosine in dimethyl sulphoxide in view of the poor solubility of L-tyrosine in water) is treated substantially by the procedure described in Example 1 (1) to give 4-(4-acetoxyphenyl)-3-phthalimidobutanoic acid in 49% yield, m.p. 151°–153.5° C.

(2) 5-(4-Acetoxyphenyl)-4-phthalimidopentanoic acid.

4-(4-Acetoxyphenyl)-3-phthalimidobutanoic acid is treated substantially by the procedure described in Example 1(2) to give 5-(4-acetoxyphenyl)-4-phthalimidopentanoic acid in 54.5% yield, m.p. 142.5°–144.5° C.

(3) 5-Amino-6-(4-hydroxhyphenyl)hexanoic acid.

5-(4-Acetoxyphenyl)-4-phthalimidopentanoic acid is treated substantially by the procedure described in Example I(3) to give methyl-6-(4-acetoxyphenyl)5-phthalimidohexanoate. Acidolytic removal of the protecting group from this compound is carried out in the presence of phenol to give crude 5-amino-6-(4-hydroxyphenyl)hexanoic acid.

EXAMPLE 4:
5-t-BUTOXYCARBONYLAMINO-6-(4-HYDROXYPHENYL)HEXANOIC ACID

The crude 5-amino-6-(4-hydroxyphenyl)hexanoic acid prepared as described in Example 3 is treated substantially by the procedure described in Example 2 to give 5-t-butoxycarbonyl amino-6-(4-hydroxyphenyl)-hexanoic acid as a gum, $\tau$(CDCl$_3$): 1.80 (1H, broad, D$_2$O-exchangeable), $\tau_A$ 3.02, $\tau_B$ 3.26 (4H, A$_2$B$_2$, J=9H$_z$), ca 5.3–6.5 (complex, partially D$_2$O-exchangeable), 7.40 (2H, d, J=6H$_z$), ca 7.5–9.0 (6H, complex), 8.65 (9H, s); $\nu_{max}$ (CHCl$_3$); 3600, 3400, ca 2600 very broad, 1710, 1515 cm$^{-1}$.

EXAMPLE 5: 4-(2-N-t-BUTOXYCARBONYL PYROLLIDYL)BUTANOIC ACID (N-t-Boc protected analogue of prolyl-glycine in which —CH$_2$CH$_2$— replaces —CONH—)

The preparation of this compound is effected by a substantially similar procedure to that described for the N-t-Boc protected phenylalanyl-glycine analogue in Examples 1 and 2 except that N-protection is effected with a t-butoxycarbonyl rather than a phthalimido group throughout.

(1) (2-N-t-Butoxycarbonylpyrollidyl)ethanoic acid.

t-Butoxycarbonylproline is treated by the procedure described in Example 1(1) to give (2-N-t-butoxycarbonylpyrollidyl)ethanoic acid in 69% yield, m.p. 98°–99.5° C.

(2) 3-(2-N-t-Butoxycarbonylpyrollidyl)propanoic acid.

(2-N-t-Butoxycarbonyl pyrollidyl)ethanoic acid is treated substantially by the procedure described in Example 1(2) to give 3-(2-N-t-butoxycarbonylpyrollidyl)-propanoic acid in 63% yield as a gum (dicyclohexylamine salt, m.p. 108.5°–109.5° C.).

(3) 4-(2-N-t-Butoxycarbonylpyrollidyl)butanoic acid.

3-2(2-N-t-Butoxycarbonylpyrollidyl)butanoic acid is treated by the procedure of (1) and (2) above to give 4-(2-N-t-butoxycarbonylpyrrolidyl)propanoic acid in ca. 23% yield as a gum, $\tau$(CDCl$_3$): $-0.16$ (1H, s, D$_2$O-exchangeable), 6.25 (1H, multiplet), 6.68 (2H, multiplet), 7.45 to ca. 8.9 (10H, complex), 8.55 (9H, s); $\nu_{max}$ (CHCl$_3$): 1710, 1680, 1400 cm$^{-1}$.

EXAMPLE 6:
5-AMINO-4-OXO-6-PHENYLHEXANOIC ACID
(Analogue of phenylalanyl-glycine in which —COCH$_2$— replaces —CONH—)

(1) BOC-NH-CH(CH$_2$C$_6$H$_5$)-COCHN$_2$

N-methylmorpholine (0.40 ml, 3.63 mmoles) is added to a stirred solution of L-Boc-phenylalanine (0.96 g, 3.63 mmoles) in dry ethyl acetate (12.00 mls). The solution is cooled to $-10°$ C. and isobutylchloroformate (0.48 ml, 3.63 mmoles) is added. After 7 minutes the mixture is filtered into an ice-cooled flask and the precipitate washed with precooled ethyl acetate (6.00 mls). An ethereal solution of diazomethane (8.00 mmoles in 75 mls) is then added and the yellow solution kept at 4° C. overnight. Evaporation of the solvents affords the pure diazoketone (1) as a yellow-orange solid, m.p. (hexane) 95°–96° C.; $\nu_{max}$ (CHCl$_3$): 2105, 1710, 1640 cm$^{-1}$.

(2) BOC-NH-CH(CH$_2$C$_6$H$_5$)-COCH$_2$Br

A solution of HBr in ethyl acetate (1.96 mls of a 0.51 M solution, diluted to 50 mls) is added over 15 minutes to a stirred solution of the diazoketone (1) (0.29 g, 1.00 mmoles) in dry ethyl acetate (10.00 mls) at $-10°$ C. The solvent is evaporated in vacuo and the residue crystallised from hexane giving the pure bromoketone (2) as white needles (0.27 g 79%), m.p. 103.5°–104° C., $\nu_{max}$(CHCl$_3$): 1705, 1490 cm$^{-1}$.

(3) BOC-NH-CH(CH$_2$C$_6$H$_5$)-COCH$_2$P$^+$(C$_6$H$_5$)$_3$Br$^-$

Triethylamine (10 $\mu$l) is added to a stirred solution of the bromoketone (2) (0.489 g., 1.43 mmoles) is sodium dried benzene (4.80 mls). Triphenylphosphine (0.375 g, 1.43 mmoles) in dry benzene (5.72 mls) is added and the solution stirred overnight at room temperature. The white crystalline deposit is collected and washed with dry ether giving the pure keto triphenylphosphonium bromide (3) (0.710 g. 82%), m.p. 92°–94° C.; $\nu_{max}$(CHCl$_3$); 1715, 1695, 1495 cm$^{-1}$.

(4) BOC-NH-CH(CH$_2$C$_6$H$_5$)-COCH=PPh$_3$

A suspension of the keto triphenylphosphonium bromide (3) (0.63 g) in ethyl acetate (27.0 mls) is stirred vigorously overnight with sodium carbonate solution (1 M, 27.0 mls). The ethyl acetate is separated and the aqueous phase extracted once more with ethyl acetate. The extracts are combined, washed with saline and dried over magnesium sulphate. Evaporation of the solvent affords the pure ylide (4) as a foam (0.54 g, 100%), $\nu_{max}$(CHCl$_3$): 1695, 1545, 1480 cm$^{-1}$.

(5) BOC-NH-CH(CH$_2$C$_6$H$_5$)-COCH$_2$CH$_2$CO$_2$C$_2$H$_5$

A solution of the ylide (4) (0.23 g, 0.44 mmoles) 4.4 ml of anhydrous dimethyl formamide and ethyl bromoacetate (0.73 g, 4.40 mmoles) is vigorously stirred under N$_2$ at 80° C. with anhydrous Na$_2$CO$_3$ (0.90 g) for 3.0 hours. The Na$_2$CO$_3$ is removed by filtration and the filtrate and washings are combined and evaporated. The residue is partitioned between ethyl acetate and water and the organic phase washed once more with water and then with saline. The solution is dried over MgSO$_4$ and evaporated giving a pale yellow gum. A portion is purified by P.L.C. using ethyl acetate:acetone:benzene (1:2:3 v/v/v) for development. Elution with ethyl acetate affords the pure ylide BOC-NH-CH-(CH$_2$C$_6$H$_5$)-COC(CH$_2$CO$_2$C$_2$H$_5$)=P(C$_6$H$_5$)$_3$ as a pale yellow gum, $\nu_{max}$(CHCl$_3$): 1725, 1695 1525, 1490, 1480 cm$^{-1}$.

The remainder of the crude alkylation product (188.0 mg, about 70% of the total) is dissolved in ethyl acetate and treated with HCl in ethyl acetate (0.77 ml of a 0.40 M solution). The solvent is evaporated affording the ylide HCl salt which is dissolved in purified acetonitrile (40 mls). Deaerated water (40 mls) is added and half the solution is electrolysed under nitrogen at 25 volts using mercury and platinum electrodes for 1.0 hours at room temperature. The cloudy solution is evaporated, redissolved in methanol (0.5 ml) and chromatographed on Sephadex LH20 (67.0×3.25 cm$^2$) using methanol as eluent. The pure keto-ester (5) (35.0 mg) is typically eluted in fractions 43 and 44 (6.0 ml fractions, 12.0 mls/hour). The remaining ylide salt is treated in the same way affording further pure keto-ester (5) (total 69.3 mg, 75% overall yield for the two steps). $\nu_{max}$(CHCl$_3$): 1720, 1705, 1490 cm$^{-1}$.

(6) BOC-NH-CH(CH$_2$C$_6$H$_5$)-COCH$_2$CH$_2$COOH.

A solution of the keto-ester (5) (16.0 mg, 0.046 mmoles) in acetone (0.39 ml) and sodium hydroxide (0.118 M, 0.39 mls) is stirred at room temperature for 2.0 hours. The solution is diluted with water and extracted once with ethyl acetate. The aqueous phase is acidified to pH 3 with citric acid and extracted thrice with ethyl acetate. The ethyl acetate is washed with water and saline and dried over magnesium sulphate. Evaporation of the solvent affords the pure keto-acid (6). (14.7 mg, 100%) as a colourless gum. $\nu_{max}$(CHCl$_3$): 1710, 1490 cm$^{-1}$. $\tau$(CHCl$_3$): 2.8 (5H, multiplet, C$_6$H$_5$), ca 3.6 broad (D$_2$O-exchangeable, COO$\underline{H}$), 4.95 (1H multiplet, D$_2$O-exchangeable, N$\underline{H}$), 5.66 (1H, multiplet, C$\underline{H}$), 6.86–7.65 (6H, complex, 3×C$\underline{H}_2$), 8.62 (9H, s, BOC—t$\underline{Bu}$).

(7) H$_2$N—CH(CH$_2$C$_6$H$_5$)—COCH$_2$CH$_2$COOH

The BOC protecting group is removed by the use of trifluoroacetic acid to give 5-amino-4-oxo-6-phenylhexanoic acid, H$_2$N—CH—(CH$_2$C$_6$H$_5$)—COCH$_2$CH$_2$COOH.

EXAMPLE 7: 5-AMINO-6-PHENYLHEXANOIC ACID.

5-Amino-2-oxo-6-phenylhexanoic acid is reduced to give 5-amino-6-phenylhexanoic acid, isolated as the hydrochloride.

EXAMPLE 8: THE USE OF 5-AMINO-6-PHENYLHEXANOIC ACID IN THE SYNTHESIS OF THE PEPTIDE ANALOGUE SER-NHCH(CH$_2$C$_6$H$_5$)CH$_2$CH$_2$CH$_2$CO-LEU-ARG-PRO-NHC$_2$H$_5$ (I) PREPARATION OF N-T-BUTOXYCARBONYL-LEU-N-TOSYL-ARG-PRO-RESIN ESTER

N-t-Butoxycarbonyl-Pro-resin ester

1% cross-linked chloromethylated Biobeads (SX1, Cl=0.5 mM/g; 5 g, 2.5 mmoles), N-t-butoxycarbonyl (Boc) -proline (0.75 g, 3.5 mmoles), triethylamine (0.42 ml, 3 mmoles) and absolute ethanol (10 ml) are mixed and the suspension is refluxed overnight. The mixture is filtered and the resin beads are thoroughly washed with ethanol, dichloromethane, 10% v/v triethylamine in dichloromethane, dichloromethane, ethanol and ether in turn. Amino acid analysis of the dried resin typically shows 0.25 mmoles/g of Boc-proline to be incorporated on the resin by an ester link.

N-t-Butoxycarbonyl-Leu-N-tosyl-Arg-Pro-resin ester

A sample of the Boc-Pro resin ester (1.8 g, 0.45 mmoles) is treated in the following procedure; all operations being performed in an all-glass vessel similar to that described by Corley. et al, Biochem, Biophys. Res. Comm 1972, 47, 1353.

(a) Wash with $CH_2Cl_2$ (3×), isopropanol (3×) and $CH_2Cl_2$ (3×) in turn.
(b) React with 40% v/v trifluoroacetic acid in $CH_2Cl_2$ (1 min) and repeat for 20 minutes.
(c) Repeat step (a)
(d) Repeat step (b)
(e) Repeat step (a). A sample is removed and tested for free amino groups with ninhydrin (Kaiser test) (strong positive result)
(f) Wash with 10% triethylamine in $CH_2Cl_2$ (2×2 min)
(g) Repeat step (a)
(h) Add a mixture of α-N-t-butoxycarbonyl-$N^G$-tosyl arginine (tosyl or Tos represents the p-toluene sulphonyl radical) (0.505 g, 1.5 mmoles) in a mixture of $CH_2Cl_2$ (11.5 ml), dimethylformamide (0.5 ml) and 0.5 ml (1.5 mmoles) of a solution of dicyclohexylcarbodiimide (DCC) (3.0 g in 5 ml $CH_2Cl_2$) and react for 2 hours.
(i) Repeat step (a). A sample is removed and subjected to the Kaiser test (negative)
(j) Wash with 10% v/v triethylamine in $CH_2Cl_2$ (2×2 min).
(k) Repeat step (a)
(l) Acetylate with acetyl imidazole (0.17 g 1.5 mmoles) in dimethylformamide (12 ml) for 2 hours.

The whole cycle of steps (a) to (l) is then repeated with the following variations:

(f) and (j) In each case a sample of resin is removed and reacted with fluorescamine to test for completeness of coupling (negative after 2 hours).

(h) The reagent used is N-t-butoxycarbonylleucine hydrate (0.38 g, 1.5 mmoles) in a mixture of $CH_2Cl_2$ (10 ml) and 1.0 ml (3.0 mmoles) of the same dicyclohexylcarbodiimide solution.

The Boc-Leu-Arg(Tos)-Pro-resin ester is thoroughly washed with $CH_2Cl_2$, isopropanol $CH_2Cl_2$ 10% triethylamine in $CH_2Cl_2$, ethanol and ether in turn, and dried (1.887 g).

(II) PREPARATION OF
O-BENZYL-SER-NHCH-($CH_2$)$C_6H_5$)-
$CH_2CH_2CH_2$CO-LEU-N-TOSYL-ARG-PRO-RESIN
ESTER

A sample of the Boc-Leu-Arg(Tos)-Pro-resin ester (0.5 g; 0.1 mmoles) is treated in two successive cycles to add the further components of the desired compound using the cycle of procedures (a) to (l) described under (i) above with the following variations.

First Cycle.

In step (h) 5-t-butoxycarbonylamino-6-phenylhexanoic acid (30.8 mg, 0.1 mmoles) in $CH_2Cl_2$ (2.5 ml) is treated with 0.1 ml (0.1 mmoles) of a stock DCC solution (1.15 g/5 ml $CH_2Cl_2$) and added to the resin. Fluorescamine is used to monitor the coupling reaction in the step (i) and although the beads still give a positive reaction after 4 hours, steps (j), (k) and (l) are proceeded with when the resin then gives a negative fluorescamine test.

Second Cycle.

In step (h) O-benzyl, N-t-butoxycarbonylserine (120 mg; 0.4 mmoles) in $CH_2Cl_2$ (2.5 ml) is treated with 0.4 ml (0.44 mmoles) of the stock dicyclohexylcarbodiimide solution and added to the resin. After 2 hours a negative fluorescamine test is obtained (a positive test is obtained after deprotection with 40% v/v trifluoroacetic acid in step (b), confirming incorporation of the modified dipeptide in the first cycle).

(III) PREPARATION OF
SER-NHCH($CH_2C_6H_5$)$CH_2CH_2CH_2$CO-LEU-ARG-
PRO-$NHC_2H_5$

The resin attached protected compound obtained in (ii) above is suspended in dimethylformamide (15 ml) and treated with ethylamine (5 ml). The suspension is then stirred overnight in a tightly stoppered reaction vessel. The mixture is filtered and the resin beads are thoroughly washed with dimethylformamide. The filtrate is chromatographed on Sephadex LH20 in dimethylformamide to give Ser(Benzyl)-NHCH($CH_2C_6H_5$)$CH_2CH_2CH_2$ CO-Leu-Arg(Tos)-Pro$NHC_2H_5$. This resin free protected compound is dissolved in refluxing anhydrous liquid ammonia (40 ml) and the solution is treated with small pieces of sodium until a faint blue colour just persists. The colour is discharged by the addition of glacial acetic acid (2 drops) and the ammonia is then evaporated off. The residue is dried in vacuo and chromatographed in turn on Sephadex G25 SF equilibrated and eluting with 50% deaerated aqueous acetic acid containing 0.01% v/v mercaptoethanol, and Whatman CM52 equilibrated in 0.05 M ammonium acetate of pH 7.0 and eluting with a linear gradient of 0.05 M to 0.5 M ammonium acetate of pH 7 to give purified Ser-NHCH($CH_2C_6H_5$)$CH_2CH_2CH_2$CO-Leu-Arg-Pro$NHC_2H_5$.

Specifically excluded from the scope of the following claims is any claim to that compound which is an analogue of the dipeptide glycylglycine in which the —CONH— group is replaced by —$CH_2CH_2$— but this exclusion does not apply to a method using this compound.

We claim:

1. A method for isosterically replacing the nitrogen atom of the linking amide group of a dipeptide of the formula:

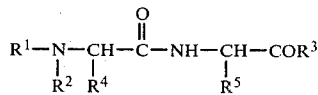

by a trivalent group

to thereby obtain a dipeptide analogue of the formula (I):

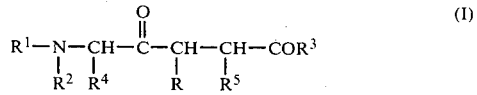

wherein R is hydrogen, or a monofunctional organic group, or a bond to the group —CH(R⁵)— forming a cyclic group

NR¹R² is an amino group, or an imino group or derivative thereof, bonded to the group —CH(R⁴)— forming a cyclic group

COR³ is a carboxyl group or a derivative thereof, R⁴ and R⁵ are the same or different side chain residues of an α-amino aicd, or R⁴ is a divalent group bonded to the group R¹R²N—, or R⁵ is a divalent organic group bonded to the group

which comprises:
reacting a ketone of the formula (II):

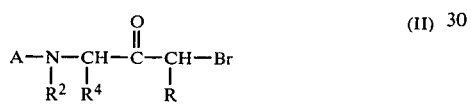

wherein A is an amine-protecting group, with zinc, to obtain a compound of formula (III):

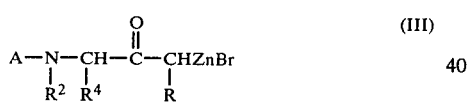

reacting the compound of formula (III) with a compound of the formula

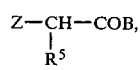

wherein Z is a group capable of acting as a leaving group in a nucleophilic substitution reaction, and B is a carboxy-protecting group to obtain a compound of the formula ANR²—CHR⁴—COCHRCHR⁵—COB;
removing the amine- and carboxy-protecting groups if necessary, thereby obtaining a compound of the formula (I).

2. A method for isosterically replacing the nitrogen atom of the linking amide group of a dipeptide of the formula:

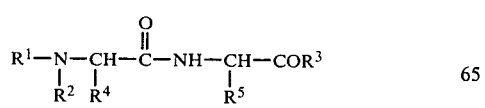

by a trivalent group

to thereby obtain a dipeptide analogue of the formula (I):

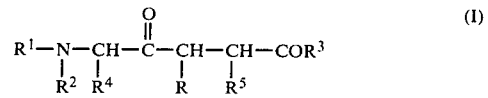

wherein R is hydrogen, or a monofunctional organic group, or a bond to the group —CH(R⁵)— forming a cyclic group

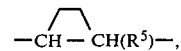

NR¹R² is an amino group, or an imino group or derivative thereof, bonded to the group —CH(R⁴)— forming a cyclic group

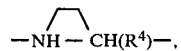

COR³ is a carboxy group or a derivative thereof, R⁴ and R⁵ are the same or different side chain residues of an α-amino acid, or R⁴ is a divalent group bonded to the group R¹R²N—, or R⁵ is a divalent organic group bonded to the group

which comprises:
reacting a compound of formula (II):

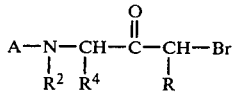

with triphenylphosphine and a mild base to obtain an ylide of formula (III):

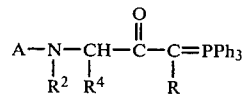

reacting the ylide of formula III with a compound of the formula

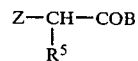

wherein Z is a group capable of acting as a leaving group in a nucleophilic substitution reaction, and B is a carboxy-protecting group, and then
cleaving the C—P bond, to thereby obtain a compound of formula (IV):

$$\begin{array}{c} \text{O} \\ \| \\ \text{A—N—CH—C—CH—CH—COB} \\ | \quad | \quad \quad | \quad | \\ \text{R}^2 \; \text{R}^4 \quad \text{R} \; \text{R}^5 \end{array} \quad \text{(IV)}$$

removing the amine- and carboxy-protecting group if necessary; and thereby
obtaining a compound of formula (I).

3. A method for isosterically replacing the nitrogen atom of the linking amide group of a dipeptide of the formula:

$$\begin{array}{c} \text{O} \\ \| \\ \text{R}^1\text{—N—CH—C—NH—CH—COR}^3 \\ | \quad | \quad \quad \quad | \\ \text{R}^2 \; \text{R}^4 \quad \quad \text{R}^5 \end{array}$$

by a methylene group —CH$_2$—, and for replacing the carbonyl group of said linking amide group by a methylene group —CH$_2$—, to thereby obtain a dipeptide analogue of the formula (I):

$$\begin{array}{c} \text{R}^1\text{—N—CH—CH}_2\text{—CH}_2\text{—CH}_2\text{—COR}^3 \\ | \quad | \\ \text{R}^2 \; \text{R}^4 \end{array} \quad \text{(I)}$$

wherein NR$^1$R$^2$ is an amino group, or an imino group or derivative thereof, bonded to the group —CH(R$^4$)— forming a cyclic group $$-\text{NH} \overset{\frown}{\quad} \text{CH(R}^4\text{)}-,$$

COR$^3$ is a carboxy group or derivative thereof, R$^4$ is the side chain residue of an α-amino acid, or R$^4$ is a divalent group bonded to the group R$^1$R$^2$N—, which comprises:
reacting an amino acid derivative selected from the group consisting of amino acid halide, amino acid imidazolylamide and amino acid anhydride, of the formula (II):

$$\begin{array}{c} \text{O} \\ \| \\ \text{A—N—CH—C—Q} \\ | \quad | \\ \text{R}^2 \; \text{R}^4 \end{array} \quad \text{(II)}$$

wherein A is an amine-protecting group, and Q is selected from the group consisting of halogen atom $$\text{N} \overset{\frown}{\underset{\smile}{\quad\quad}} \text{N—}$$

group and oxocarbonyl-containing group, with diazomethane to obtain an α-diazomethyl compound of formula (III):

$$\begin{array}{c} \text{O} \\ \| \\ \text{A—N—CH—C—CHN}_2 \\ | \quad | \\ \text{R}^2 \; \text{R}^4 \end{array} \quad \text{(III);}$$

reacting said compound of formula (III) with a catalyst and an alcohol of formula R$^6$OH wherein R$^6$ is a C$_1$-C$_6$ alkyl group, to yield an ester of formula (IV):

$$\begin{array}{c} \text{O} \\ \| \\ \text{A—N—CH—CH}_2\text{—C—OR}^6 \\ | \quad | \\ \text{R}^2 \; \text{R}^4 \end{array} \quad \text{(IV)}$$

transforming the ester of formula (IV) to an α-diazomethyl ketone of formula (V):

$$\begin{array}{c} \text{O} \\ \| \\ \text{A—N—CH—CH}_2\text{—C—CHN}_2 \\ | \quad | \\ \text{R}^2 \; \text{R}^4 \end{array} \quad \text{(V)}$$

reacting said α-diazomethyl ketone of formula (V) with a catalyst and an alcohol to yield an ester of formula (VI):

$$\begin{array}{c} \text{O} \\ \| \\ \text{A—N—CH—CH}_2\text{—CH}_2\text{—C—OR}^6 \\ | \quad | \\ \text{R}^2 \; \text{R}^4 \end{array} \quad \text{(VI)}$$

transforming said ester of formula (VI) to an α-diazomethyl ketone of formula (VII):

$$\begin{array}{c} \text{O} \\ \| \\ \text{A—N—CH—CH}_2\text{CH}_2\text{—C—CHN}_2 \\ | \quad | \\ \text{R}^2 \; \text{R}^4 \end{array} \quad \text{(VII)}$$

reacting said α-diazomethyl ketone of formula (VII) with a catalyst and an alcohol R$^6$OH to yield an ester of formula (VIII):

$$\begin{array}{c} \text{A—N—CH—CH}_2\text{CH}_2\text{CH}_2\text{—COOR}^6 \\ | \quad | \\ \text{R}^2 \; \text{R}^4 \end{array} \quad \text{(VIII)}$$

removing the amino protecting group and transforming the carboxy ester to a group COR$^3$ if necessary:
thereby obtaining a dipeptide analogue of formula (I).

4. A method for isosterically replacing the nitrogen atom of the linking amide group of a dipeptide of the formula:

$$\begin{array}{c} \text{O} \\ \| \\ \text{R}^1\text{—N—CH—C—NH—CH—COR}^3 \\ | \quad | \quad \quad \quad | \\ \text{R}^2 \; \text{R}^4 \quad \quad \text{R}^5 \end{array}$$

by a trivalent group $$\begin{array}{c} | \\ -\text{CR—}, \end{array}$$

and for replacing the carbonyl group of said linking amide group by a methylene group —CH$_2$—, to thereby obtain a dipeptide analogue of the formula (I):

$$\begin{array}{c} \text{R}^1\text{—N—CH—CH}_2\text{CH—CH—COR}^3 \\ | \quad | \quad \quad | \quad | \\ \text{R}^2 \; \text{R}^4 \quad \text{R} \; \text{R}^5 \end{array} \quad \text{(I)}$$

which comprises:
preparing a dipeptide analogue of formula (II):

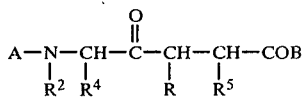

according to the process of any of claims 1 or 2, wherein the symbols A, $R^1$, $R^2$, $R^3$, $R^4$, $R^5$, and B have the meaning given in said claims;

reducing said compound of formula (II) to a compound of formula (III):

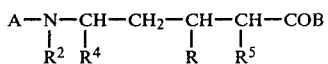

removing the amino- and carboxy-protecting groups if necessary, thereby obtaining a compound of formula (I).

5. A process of preparing a polypeptide analogue which comprises: preparing a dipeptide analogue of formula (I):

$$R^1-N(R^2)-CH(R^4)-\overset{O}{\underset{\|}{C}}-CH(R)-CH(R^5)-COR^3 \quad (I)$$

by the process of any of claims 1 or 2, wherein $R^1$, $R^2$, $R^3$, $R^4$, $R^5$ R have the meanings given in said claims, adding at least one α-amino acid or a polypeptidyl residue comprising a sequence of α-amino acids to the amino terminus or to the carboxy terminus or to both, of said dipeptide analogue.

6. A process of preparing a polypeptide analogue which comprises:

preparing a dipeptide analogue of formula (I):

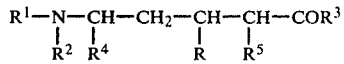

by the process of claim 4, wherein $R^1$, $R^2$, $R^3$, $R^4$, $R^5$ and R have the meanings given in said claims, adding at least one α-amino acid or a polypeptidyl residue comprising a sequence of α-amino acids to the amino terminus or the carboxy terminus or to both, of said dipeptide analogue.

7. A process of preparing a polypeptide analogue which comprises: preparing a dipeptide analogue of formula (I):

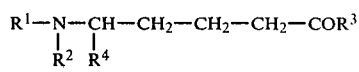

by the process of claim 3, wherein $R^1$, $R^2$, $R^3$ and $R^4$ have the meanings given in said claim;

adding at least one α-amino acid or a polypeptidyl residue comprising a sequence of α-amino acids to the amino terminus or to the carboxy terminus or to both, of said dipeptide analogue.

8. The method of any of claims 1, 2 or 3 wherein $R^4$ and $R^5$ are the same or different side chain residues of an α-amino acid selected from the group consisting of α-alanine, β-alanine, arginine, asparagine, aspartic acid, 3,5-dibromotyrosine, cystine, cysteine, dopa, N-formyl glycine, glycine, glutamic acid, glutamine, histidine, hydroxylysine, hydroxyproline, 3,5-diiodotyrosine, isoleucine, leucine, lysine, methionine, ornithine, phenylalanine, proline, pyroglutamic acid, hydroxyproline, serine, spinacin, threonine, thyroxine, tryptophan, tyrosine and valine.

9. The method of any of claims 1, 2 or 3 wherein said amine-protecting group A is selected from the group consisting of benzyloxycarbonyl, p-methoxybenzyloxycarbonyl, amyloxycarbonyl, biphenylisopropoxycarbonyl, o-nitrophenylsulfonyl, phthaloyl, and p-butoxycarbonyl.

10. The method of any of claims 1 or 2 wherein said carboxy protecting group B is selected from the group consisting of $C_1$–$C_4$ alkyl esters, amides, N-substituted amides, benzyl esters and t-butylester.

11. The method of any of claims 1 or 2 wherein said leaving group Z is selected from the group consisting of p-toluene sulphonate and bromide.

12. The method of any of claims 1, 2 or 3 which comprises removing the amino-protecting group A by acid hydrolysis.

13. The method of claim 2 wherein said mild base is $Na_2CO_3/H_2O/C_2H_5OCOCH_3$.

14. The method of claim 2 wherein said cleavage of said C—P bond is carried out by electrolysis.

15. The method of claim 4 wherein said reduction of said compound of formula (II) is carried out by $HSCH_2CH_2SH$ followed by treatment with Raney nickel.

16. The method of claim 4, wherein said reduction of said compound of the formula (II) is carried out by a stepwise reduction which comprises:

converting the grouping —COB, to a group —COOH;

reducing the keto group to an alcohol;

activating said alcohol group by transforming said alcohol group into a mesylate or tosylate thereof; and selectively reducing the activated alcohol group with a hydride reagent.

17. A dipeptide analogue of the formula:

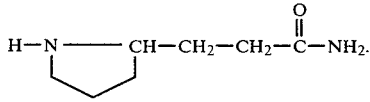

18. A polypeptidue analogue of the formula:

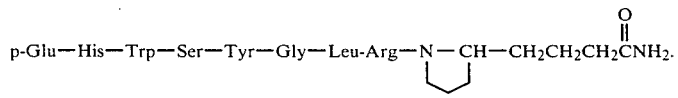

19. A polypeptidue analogue of the formula:

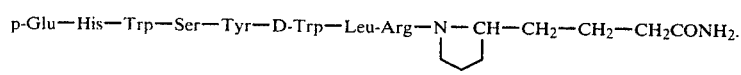
* * * * *